United States Patent [19]

Pearlman

[11] Patent Number: 5,199,438
[45] Date of Patent: Apr. 6, 1993

[54] MEASUREMENT OF CARDIAC PERFORMANCE

[75] Inventor: Andrew L. Pearlman, Misgav, Israel

[73] Assignee: ATP Advanced Technologies Limited, Vaduz, Liechtenstein

[21] Appl. No.: 565,642

[22] Filed: Aug. 10, 1990

[30] Foreign Application Priority Data

Sep. 27, 1989 [IL] Israel .................................... 091803

[51] Int. Cl.$^5$ ................................................ A61B 5/02
[52] U.S. Cl. .................................... 128/670; 128/693; 128/713; 128/700
[58] Field of Search ............... 128/668, 670, 671, 693, 128/700, 707, 713

[56] References Cited

U.S. PATENT DOCUMENTS

| | | | |
|---|---|---|---|
| 4,137,910 | 2/1979 | Murphy | 128/713 |
| 4,493,210 | 1/1985 | Hassler | 128/661.1 |
| 5,074,310 | 12/1991 | Mick | 128/748 |

OTHER PUBLICATIONS

*Rate of Change of Ventricular Power: An Indicator of Ventricular Performance during Ejection*, Stein and Sabbab, American Heart Journal Feb. 1976, vol. 91, No. 2, pp. 219-227.

*Left Ventricular Power in Man*, Russell et al., American Heart Journal, vol. 81, No. 6, pp. 799-808, Jun. 1971.

Ventricular Performance Measured during Ejection: Studies in Patients of the Rate of Change of Ventricular Power, Stein and Sabbah, American Heart Journal, vol. 91, No. 91, No. 5, May 1976, pp. 599-606.

*Method for Noninvasive Measurement of Central Aortic Systolic Pressure*, Marmur et al., Clinical Cardiology, 10, 215-221-1987.

Primary Examiner—Lee S. Cohen
Assistant Examiner—Robert L. Nasser, Jr.
Attorney, Agent, or Firm—Christie, Parker & Hale

[57] ABSTRACT

The value of the cardiac power index of a functioning heart is determined noninvasively. The index is the second time derivative of the work performed by the left ventricle of the heart between the onset of systole and a point of maximum left ventricular power. Left ventricular work is the product of left ventricular pressure and left ventricular volume. Left ventricular volume can be measured noninvasively by use of gamma camera technology. Left ventricular pressure can be measured noninvasively at a selected arterial location, such as the brachial artery, displaced in the body form the heart. Cardiac pressure pulses can be measured at the arterial location by use of a Doppler ultrasound sensor and processor with compensation for the time delay in the arrival of the pulses from the heart at that location. Ventricular volume and pressure measurements are made at a number of pressure values during several cardiac cycles and the measurements of pressure so obtained are suitably averaged to eliminate motion artifacts from those measurements.

35 Claims, 18 Drawing Sheets

FIG. 7A

Flow Chart of Operation of Cardiac Monitor

STEPS
10-20:        PATIENT AND EQUIPMENT SETUP

10   Inject Gamma tracer, set up patient on Gamma Camera. Attach ECG electrodes, blood pressure monitor, pressure waveform sensor.

20   Visually verify acceptable ECG and pressure waveform acquisition on video display. Verify acceptable Gamma Camera operation.

30         OPERATOR REQUESTS MEASUREMENT INITIALIZATION 40-90       MEASUREMENT INITIALIZATION

40   Measure MAXAMP, MINAMP, Propagation time.
For each of 10 consecutive cardiac cycles:

- measure the maximum and minimum pressure waveform values, MAXAMP and MINAMP.
- Use PROCEDURE ARRIVAL to calculate propagation time, PropTime.

50   Obtain diastolic and systolic pressures, and heart rate measurements from MIBP monitor.

60   Calculate DP = (Systolic-Diastolic).

70   Calculate Cuff Pressure settings:

$$P0 = 1.25 * \text{Systolic}$$
$$P1 = \text{Systolic}$$
$$P2 = \text{Systolic} - 0.25 * DP$$
$$P3 = \text{Systolic} - 0.50 * DP$$
$$P4 = \text{Systolic} - 0.65 * DP$$
$$P5 = \text{Systolic} - 0.75 * DP$$
$$P6 = \text{Systolic} - 0.85 * DP$$
$$P7 = \text{Systolic} - 0.90 * DP$$
$$P8 = \text{Systolic} - 0.95 * DP$$
$$P9 = \text{Diastolic}$$

80-90   Measure No-Flow Baseline Pulse Waveform Values.

80   Inflate cuff 38 to P0.

90   REPEAT

Calculate cumulative average pressure waveform amplitude AMP for 10 seconds

FIG. 7B

Reset CUFF_PRESSURE_INCREMENT_FLAG if (AMP > = 0.05* (MAXAMP-MINAMP))
- ○ increase cuff pressure by 10%
- ○ Set Cuff _PRESSURE _INCREMENT _FLAG UNTIL CUFF_PRESSURE_INCREMENT_FLAG not set.

| | |
|---|---|
| 100-260 | CPI MEASUREMENT |
| 100-160 | MEASUREMENT OF BLOOD PRESSURE AS A FUNCTION TO TIME |
| 100 | For i = 1 to 8 Set Cuff Pressure to next value Pi. |
| 110 | For j = l to N (N is typically 5 - 10) |
| 112 | After new pressure reached, detect next QRS complex. |
| 114 | Apply PROCEDURE ARRIVAL to find breakthrough time, store in element PressureTime (i,j) of array PressureTime. |

NEXT j

| | |
|---|---|
| 120 | Replace outlying PressureTime points with clustered ones, calculate average time for each pressure and store in array PressurePoints. |

REPEAT

| | |
|---|---|
| 122 | Calculate average TIMEAVE and standard deviation TDEV of elements |

PressureTime (i,k), k = 1 to N.

| | |
|---|---|
| 124 | Reset REPLACED_POINT |
| 126 | Find the first PressureTime (i,k), k = 1 to N, that lies outside the range of [TIMEAVE +/- 3*TDEV]. If such a point is found: |

- ○ Delete it from PressureTime array.
- ○ Replace it by taking a new measurement (steps 112, 114)
- ○ Set REPLACED_POINT flag.

UNTIL REPLACED_POINT flag not set.

FIG. 7C

130    Now fill array PressurePoints with the arrival time shifted by progatation time, PropTime, and the corresponding cuff pressures.

$$PressurePoints\ (i,1) = Pi;$$

$$PressurePoints\ (i,2) = TIMEAVE - PropTime$$

NEXT i (Cuff Pressure setting)

140   PressurePoints (9,1) = P9  (i.e., Diastolic Value)

150   PressurePoints (9,2) = 0

160   Interpolate the values of array PressurePoints using a piecewise polynomial least squares fit to the sampled pressure-time pairs to obtain a pressure value for each millisecond after the start of systole, and store each in array PressureCurve.

180-190    LEFT VENTRICULAR VOLUME DETERMINATION

180   Obtain the sampled volumetric values and post-QRS measurement times from the Gamma Camera via its CPU, storing in array VolumePoints.

190   Interpolate the values of array VolumePoints using a piecewise polynomial interpolation function, and store the values for each millisecond post-QRS in array VolumeCurve.

200-260    CALCULATE CARDIAC POWER CURVE AND CPI

200   Starting with i = 1 to K sample points (K typically the number of milliseconds during the systolic rise)

$$WORK(i) = PressureCurve(i) * VolumeCurve(i)$$

210   WORK(0) = WORK(1)

For i=1 to K, calculate derivative of WORK(i), typically using central difference method;

$$POWER(i) = WORK(i+1) - WORK(i-1)/2$$

220    Search POWER(i) for maximum power value MAXPOWER at time, IMAX

230    Fit a least square linear regression to all points in POWER from i=1 to IMAX; calculate the standard deviation of the data from the fitted line.

FIG. 7D

240   For = 1 to K, delete any entries from POWER(i) which have values outside 3 standard deviations from the fitted line. If points have been deleted, return to 220.

250   Fit a least squares linear regression to all points.

260   Final CPI value is the slope of said linear regression.

PROCEDURE ARRIVAL: Measure Propagation Time

With A/D converter 44 sampling at least 1000 samples per second

1   Detect the time, TQRS, of the R-wave trigger 2   start clock counting 3   wait 50 milliseconds 4   from the subsequent 30 milliseconds' samples, calculate the mean LOWMEAN and standard deviation LOWSD and fit a least squares linear regression, LOWLINE to said samples 5   detect the first 30 consecutive points whose values are all greater than (LOWMEAN = 3*LOWSD)

6   fit a least squares regression line HIGHLINE to said 30 msec of points 7   calculate start of systolic, TSYS1 as the time when LOWLINE and HIGHLINE intersect 8   calculate the number of milliseconds from TQRS to TSYS1.

Fig. 11B
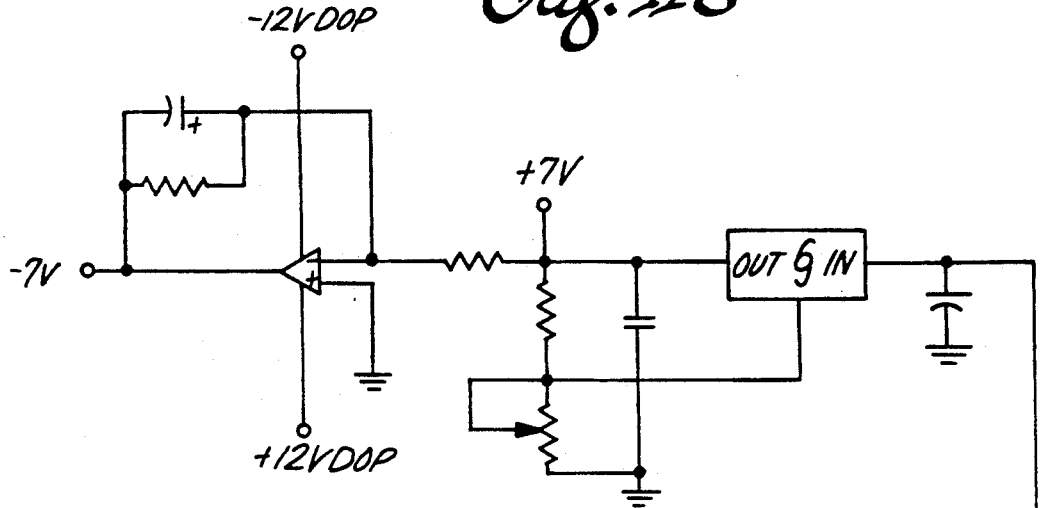
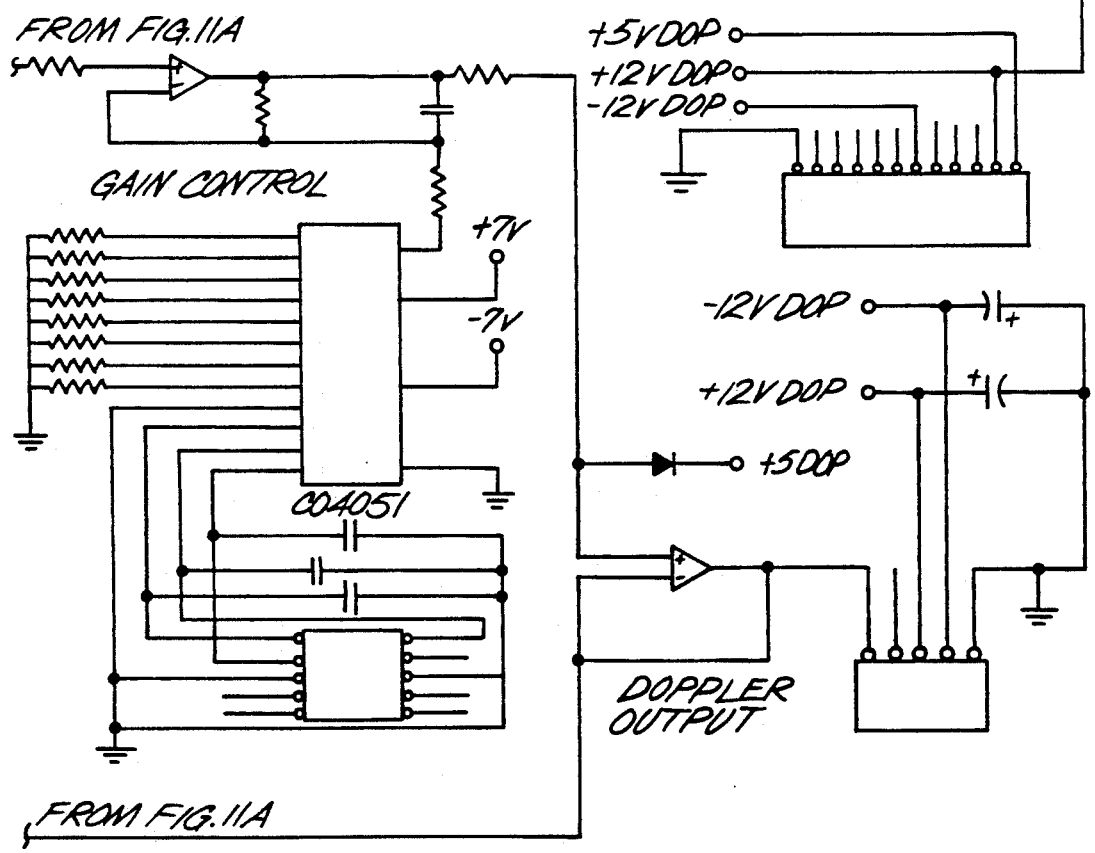

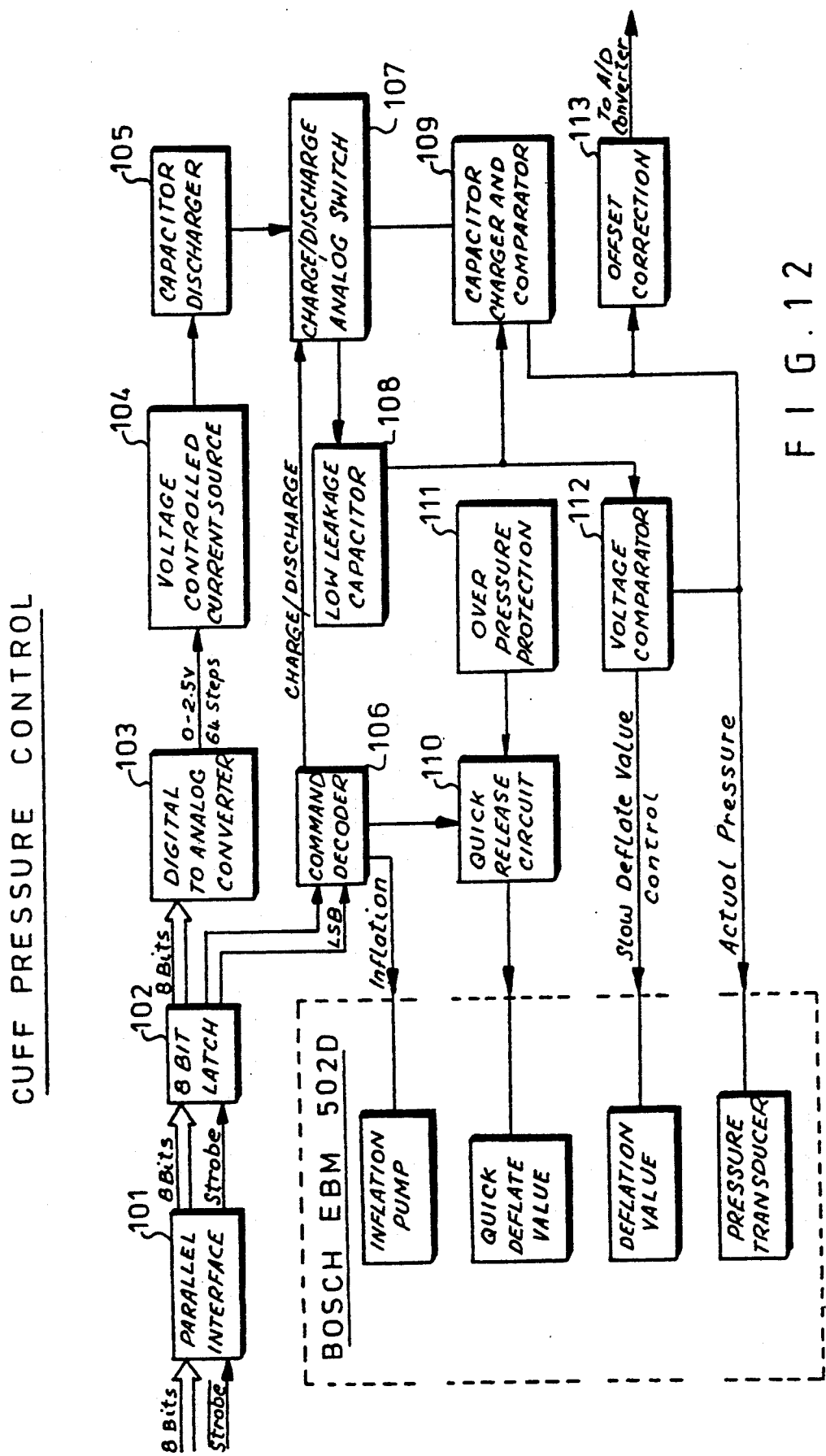

MEASUREMENT OF CARDIAC PERFORMANCE

FIELD OF THE INVENTION

The present invention relates to cardiac monitors generally and more particularly to cardiac monitors which measure left ventricular performance.

BACKGROUND OF THE INVENTION

Various cardiac monitors are known in the art. The known monitors typically utilize measurements taken invasively using cardiac catheterization or noninvasively. The prior art is summarized in an article entitled "Method for Noninvasive Measurement of Central Aortic Systolic Pressure," by A. Marmor, et al., *Clinical Cardiology*, 1987, 10:215, and the references cited therein.

SUMMARY OF THE INVENTION

The present invention seeks to provide an improved cardiac monitor and method for cardiac monitoring.

There is thus provided in accordance with a preferred embodiment of the present invention a method for reliably measuring cardiac performance under resting and/or exercise stress conditions to enable measurement of the cardiac power index including the steps of measuring the left ventricular pressure:

measuring the left ventricular volume;

determining the product of the left ventricular pressure and the left ventricular volume as a function of time;

determining the time derivative of the product; and determining the slope of the time derivative, as it rises thereby to provide an indication of the cardiac power index, characterized in that the step of measuring the left ventricular pressure includes the step of:

measuring the arrival times of cardiac pressure pulses at a given site at a plurality of pressure values, especially a set of optimized pressure values.

Further in accordance with an embodiment of the present invention the method is further characterized in that the step of measuring the left ventricular pressure also comprises the step of employing an optimization algorithm which concentrates the largest number of pressure measurements in the interval during the early ejection phase.

Additionally in accordance with a preferred embodiment of the present invention, the method is additionally characterized in that the step of measuring the left ventricular pressure also comprises the step of measuring the arrival times of cardiac pressure pulses at a given site during the time period during which the left ventricular pressure rises from 100% to 125% of the end-diastolic value.

The method may also comprise the step of displaying real-time electrocardiogram and blood pressure wave forms on a continuously updated basis.

There is also provided a method for reliably measuring cardiac performance under resting and/or exercise stress conditions to enable measurement of the cardiac power index including the steps of:

measuring the left ventricular pressure and the left ventricular volume;

determining the product of the left ventricular pressure and the left ventricular volume as a function of time;

determining the time derivative of said product; and determining the slope of the time derivative, as it rises thereby to provide an indication of the cardiac power index, characterized in that it also includes the step of displaying real-time electrocardiogram and blood pressure wave forms on a continuously updated basis.

In accordance with a preferred embodiment of the invention, the method is also characterized in that it includes the steps of displaying, simultaneously and together with said electrocardiogram and brachial pressure wave forms, the calculated delayed left ventricle pressure values and the calculated corresponding left ventricular volumetric values.

Additionally in accordance with a preferred embodiment of the invention, the method is further characterized in that it comprises the step of measuring, during one or more cardiac cycles, the arrival time for the given occlusive pressure, and storage of the measured times for each pressure.

Further in accordance with an embodiment of the present invention, the step of measuring the time of arrival includes the step of rejecting time values having unacceptable variance.

Additionally in accordance with a preferred embodiment of the invention, the step of measuring the time of arrival also includes the step of statistical averaging of several acceptable sample points to reduce the effects of beat-to-beat variance, artifactual signals and noise.

Further in accordance with an embodiment of the invention, the step of measuring left ventricular volume includes the steps of taking least one measurement within 15 msec of QRS.

Additionally in accordance with an embodiment of the invention, the step of measuring left ventricular volume includes the steps of carrying out multiple volume measurements within 40 msec of each other.

Further in accordance with an embodiment of the invention, the method is further characterized by the steps of measuring the systolic and diastolic blood pressure.

In accordance with a preferred embodiment of the invention, there is also provided the step of calculating the cardiac power index as the slope of the best least squares regression fit to an entire set of instantaneous power values up to a maximum power point, excluding points whose values lie outside the range of variance that is commensurate with the other points.

Another preferred embodiment of the inventive method relates to a method of measurement of the left ventricular pressure as a function of time, i.e., according to this embodiment not the cardiac power index based on the product of pressure and volume as a function of time is ascertained, rather the arrival times of cardiac pressure pulses at a given site at a plurality of pressure values, especially a set of optimized pressure values, are measured, and indices from said arrival times at said plurality of pressure values are derived, including but not limited to the time derivative of the pressure. These indices can be taken or evaluated for the characterization of cardiac performance.

The measured arrival times are preferably used for fitting a curve, said curve estimating the time varying wave form of the left ventricular pressure. The slope of the curve is calculated and defines one of the preferred indices.

An especially preferred embodiment of the inventive method resides in measuring the arrival times by measurement of Doppler signals of blood flow at the given site. For this a specific Doppler ultrasound sensor and processor are used which are described below.

The inventive method has the advantage that cardiac performance can be reliably measured under exercise stress conditions of the patient. This is especially achieved by the Doppler blood flow measuring method used together with a very specific processing of the received Doppler signals which results in a clear and noise-free characterization of the cardiac performance, i.e., pressure and volume-time or pressure-time curves.

Additionally in accordance with an embodiment of the invention, there is provided an apparatus for reliably measuring cardiac performance under resting and/or exercise stress conditions to enable measurement of the cardiac power index comprising:

apparatus for measuring the left ventricular pressure;
apparatus for measuring the left ventricular volume;
apparatus for determining the product of the left ventricular pressure and the left ventricular volume as a function of time;
apparatus for determining the time derivative of said product; and
apparatus for determining the scope of the time derivative, as it rises thereby to provide an indication of the cardiac power index,
characterized in that the apparatus for measuring the left ventricular pressure comprises apparatus for measuring the arrival times of cardiac pressure pulses at a given site at a plurality of pressure values, especially a set of optimized pressure values.

Further in accordance with an embodiment of the invention, the apparatus for measuring the left ventricular pressure also comprises apparatus for employing an optimization algorithm which concentrates the largest number of pressure measurements in the interval during the early ejection phase.

Additionally in accordance with an embodiment of the invention, the apparatus is additionally characterized in that the apparatus for measuring the arrival times of cardiac pressure pulses at a given site during the time period during which the left ventricular pressure rises from 100% to 125% of the end-diastolic value.

Additionally in accordance with an embodiment of the present invention, there is also provided apparatus for displaying real-time electrocardiogram and blood pressure wave forms on a continuously updated basis.

Further in accordance with an embodiment of the present invention, there is provided apparatus for reliably measuring cardiac performance under resting and-/or exercise stress conditions to enable measurement of the cardiac power index comprising:

apparatus for measuring the left ventricular pressure and the left ventricular volume;
apparatus for determining the product of the left ventricular pressure and the left ventricular volume as a function of time;
apparatus for determining the time derivative of said product; and
apparatus for determining the slope of the time derivative, as it rises thereby to provide an indication of the cardiac power index,
characterized in that it also includes apparatus for displaying real-time electrocardiogram and blood pressure wave forms on a continuously updated basis.

Additionally in accordance with a preferred embodiment of the present invention, the apparatus is also characterized in that it includes apparatus for displaying, simultaneously and together with said electrocardiogram and brachial pressure wave forms, calculated delayed left ventricle pressure values and calculated corresponding left ventricular volumetric values.

Additionally in accordance with a preferred embodiment of the present invention, the apparatus is further characterized in that it comprises apparatus for measuring, during one or more cardiac cycles, the arrival time for the given occlusive pressure, and storage of the measured times for each pressure.

Further in accordance with a preferred embodiment of the present invention, the apparatus for measuring the time of arrival includes apparatus for rejecting time values lying outside the range of variance of the other values.

Further in accordance with an embodiment of the present invention, the apparatus for measuring the time of arrival also includes apparatus for statistical averaging of several acceptable sample points to reduce the effects of beat-to-beat variance, artifactual signals and noise.

Additionally in accordance with a preferred embodiment of the present invention, the apparatus of measuring left ventricular volume includes apparatus for taking at least one measurement within 15 msec of QRS.

Further in accordance with a preferred embodiment of the present invention, the apparatus for measuring left ventricular volume includes apparatus for carrying out multiple volume measurements within 40 msec of each other.

Additionally in accordance with a preferred embodiment of the present invention, there is also provided apparatus for measuring the systolic and diastolic blood pressure.

Additionally in accordance with a preferred embodiment of the present invention, there is also provided a pulse wave sensor and/or pulse wave processor with reduced motion artifact effects.

Further in accordance with a preferred embodiment of the invention, the apparatus for detecting the arrival of the cardiac pressure waves at a given site, preferably at the brachial artery site, is a Doppler ultrasound arterial wall motion sensor.

According to an especially preferred embodiment of the inventive apparatus, the means for detecting the arrival of the cardiac pressure waves at a given site, preferably at the brachial artery site, is a Doppler ultrasound blood flow sensor. The sensor itself and a corresponding processing unit combined therewith allow the rejection of motion artifact effects.

The Doppler ultrasound sensor (transducer) is advantageously held by an armband mount comprising an adjustable transducer mount fixed to an adjustable attachment strap. The Doppler ultrasound sensor (transducer) is preferably formed as a flat package with Doppler crystals mounted so as to provide fixed angle of illumination, typically 30° to horizontal.

Said pulse wave processor preferably contains a high-pass filter separating the high frequencies from the audio signal and an RMS-amplitude-to-DC converter measuring the power of the high frequency spectrum by converting the total RMS (root mean square) into a proportional DC voltage.

BRIEF DESCRIPTION OF THE DRAWINGS

The present invention will be understood and appreciated more fully from the following detailed description, taken in conjunction with the drawings in which:

FIG. 7 (comprised of FIGS. 7A–7D) is a flow chart describing the operation of the apparatus shown in FIGS. 1–6;

FIG. 12 is a block diagram of a cuff pressure control unit; and

DETAILED DESCRIPTION OF THE PRESENT INVENTION

In an article entitled, "Noninvasive Assessment of Myocardial Performance," by A. Marmor, et al., published in the *Journal of Nuclear Medicine*, vol. 30, No. 10, Oct. 1989, the authors define a measure of cardiac performance known as the ejection rate of change of power, which is referred to herein as the cardiac power index or CPI. CPI represents the rate at which cardiac power changes during the period of ejection of blood from the heart, known as early systole, and is estimated from the cardiac power curve. The cardiac power curve is obtained by taking the time derivative of the product of the cardiac left ventricular pressure and volume during the early part of systole.

Figure 1:
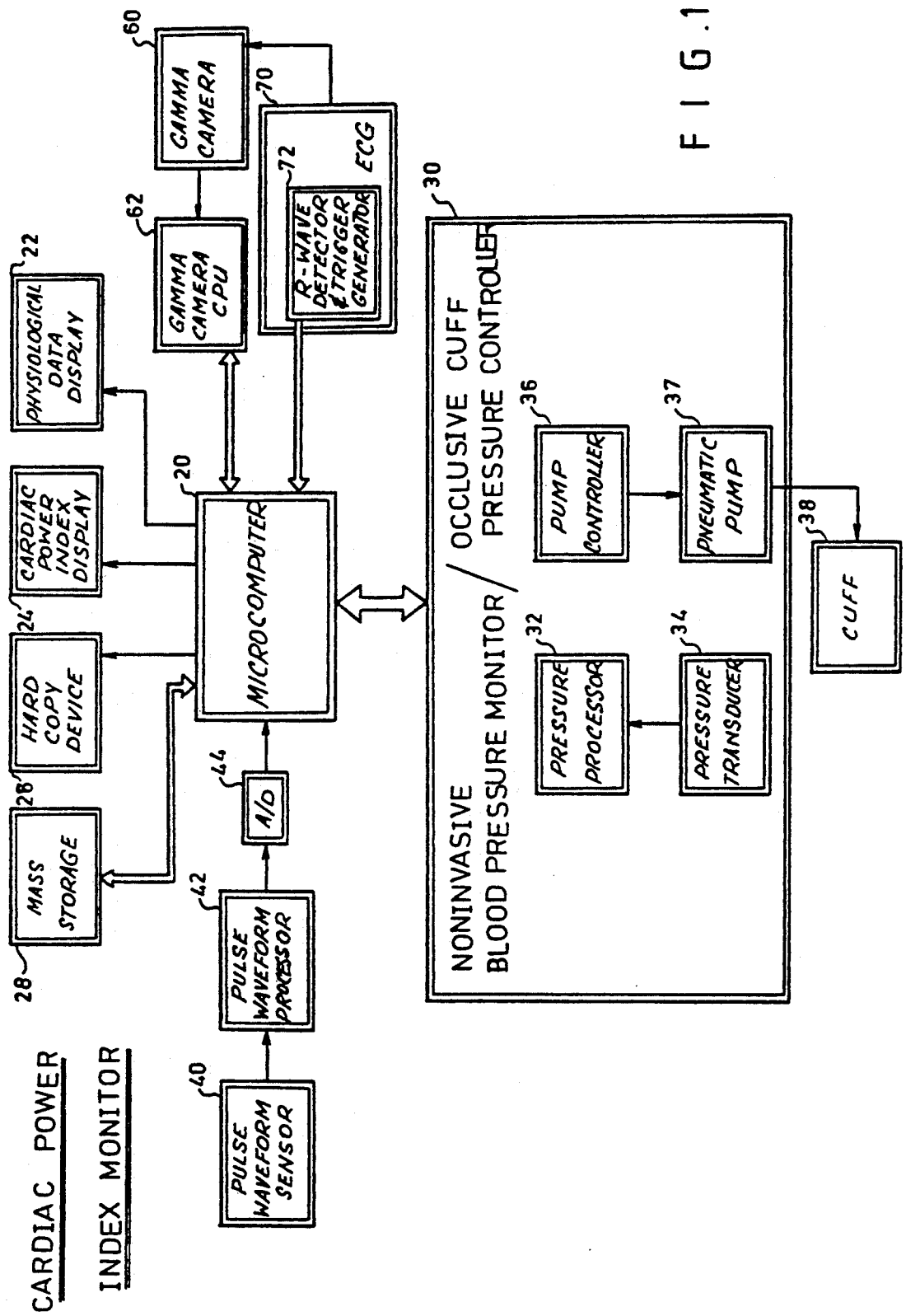
FIG. 1 is a functional block diagram of the cardiac power index monitor (CPIM) constructed and operative in accordance with a preferred embodiment of the present invention.
Figure 2:
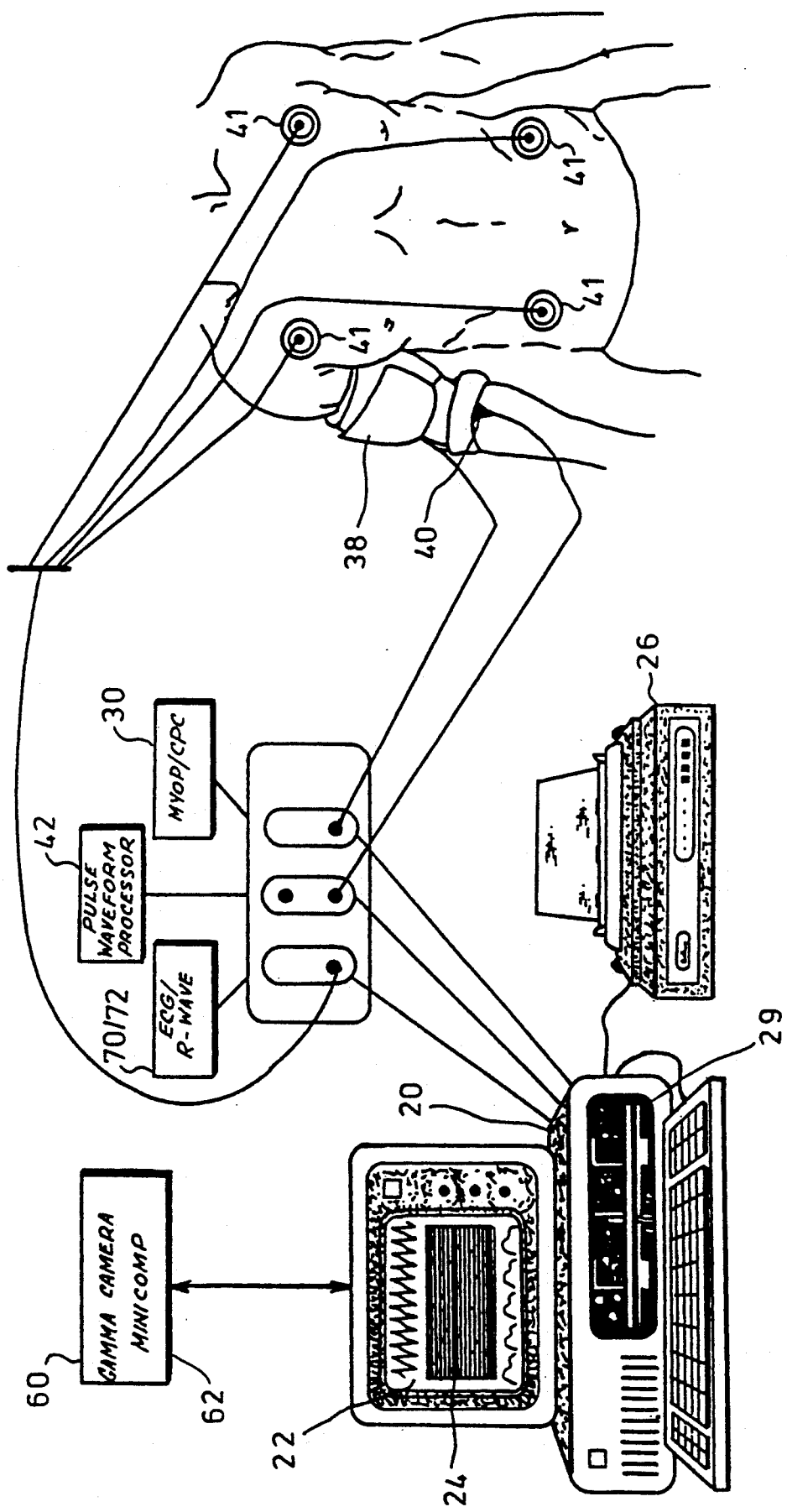
FIG. 2 illustrates a system implementation based on the embodiment of FIG. 1.

Reference is now made to FIG. 1 which illustrates, in block diagram form, a cardiac power index monitor, constructed and operative in accordance with the present invention. Reference is also made to FIG. 2, which illustrates a system implementation based on the embodiment of FIG. 1. The cardiac monitor, denoted by reference numeral 10, comprises a microcomputer 20, which is preferably IBM-PC compatible. The microcomputer 20 preferably controls all monitor functions and drives a physiological data display 22, such as an EGA graphics video monitor, and a cardiac power index (CPI) display 24, which may be provided by the same apparatus used for display 22. The microcomputer 20 also stores data in and retrieves data from a mass storage device 28, preferably a hard disk drive with at least 10 mbytes, and drives a hard copy device 26, preferably an Epson compatible dot-matrix printer.

The monitor of FIG. 1 also comprises noninvasive blood pressure measurement (NIBP)/cuff pressure controller (CPC) apparatus 30, such as a Bosch EBM 502 D, for measuring the brachial arterial pressure and heart rate, and which operates a sphygmomanometric cuff 38. Cuff 38 is preferably a wrap-around type such as that used in the PediSphyg system by CAS Medical, Inc. of Branford, Conn., U.S.A., or a Bosch cuff. The cuff pressure controller incorporates appropriate interface and control circuitry and software to enable the operation of apparatus 30 in the mode of pressure control of cuff 38 instead of its conventional mode of operation for blood pressure measurement. A block diagram of the controller is shown in FIG. 12.

The monitor 10 also includes an ECG monitor 70 and an R-wave detector and trigger generator 72, both typically contained in standard ECG monitor system such as a Mennen Horizon 2000 patient monitor.

Also included in monitor 10 is a pulse wave form sensor 40, namely, a Doppler ultrasound wall motion and blood flow detection sensor, such as MedaSonics model 94G, attached to the same arm as the cuff 38, and approximately 1–3 cm distal to it. A pulse waveform processor 42 (shown in FIG. 10), preferably an analog and/or digital circuit whose input is the waveform from sensor 40, provides an analog output which is preferably proportional to the blood flow.

Alternatively, the output may be proportional to the wall motion or the velocity of wall motion. In either implementation, high-pass filters eliminate most of the influence of motion artifacts from the output signal to the A/D converter 44, whose digital data output is read by microcomputer 20.

A gamma camera 60, which may be a commercial field-of-view gamma camera, such as an Elscint Model APEX and its associated CPU 62, receives a gatling R-wave trigger either from an ECG monitor 70 or from its own internal ECG monitor. In response thereto, camera 60 records a plurality of frames of several milliseconds duration at intervals of typically 25–40 milliseconds throughout each cardiac cycle, averaging together the frames from many (typically 300) cycles to obtain the averaged volumetric frame values along the time curve through the cardiac cycle.

A gamma camera CPU 62 communicates the resulting data values to microcomputer 20 via a digital link, preferably RS232 or Centronics parallel, or alternatively via disk transfer.

As illustrated in FIG. 2, cuff 38 is attached preferably above an elbow, and is controlled by microcomputer 20 via cuff pressure controller 30. An R-wave detector and trigger generator 72 senses the sharp spike-like wave of the ECG, known as the QRS complex, and provides a digital trigger pulse corresponding to the occurrence of the R-wave (the center of the QRS spike).

It is proposed in the article by A. Marmor, et al., of Annex A to measure a cardiac power curve and from it to calculate a cardiac power index. Cardiac power is defined as the time derivative of the product of cardiac volume and cardiac (or aortic) pressure with time. The cardiac power index is defined as the slope of the portion of the power versus time curve from onset of systole to the moment of maximal power.

Determination of the cardiac power curve and cardiac power index (CPI) using the cardiac monitor 10 is described hereinbelow.

ESTIMATION OF LEFT VENTRICULAR PRESSURE

Occlusion of brachial flow during most of the cardiac cycle creates a standing fluid column between the aorta and the brachial artery, such that the rising intra-aortic pressure wave form is transmitted to the brachial artery with minimal distortion. Accordingly, the pressure values obtained at the brachial artery very closely represent those in the left ventricle.

In order to enable later combination with left ventricular volume measurements made at the heart, the brachial pressure values must be shifted in time to account for the propagation of the cardiac pressure wave from the heart to the brachial artery. The post-QRS time required for a cardiac pressure wave to travel from the heart to the brachial artery measurement site is known herein as the propagation time, as is discussed below in conjunction with FIG. 5. The propagation time for a given patient during the examination period is presumed constant under all conditions of heart activity.

The operation of the cardiac monitor 10, including the calculation of the CPI, is described in the flow chart of FIG. 7. Patient preparations for gamma camera ventriculography are completed, and 3-4 ECG electrodes 41 are attached in standard thoracic montage, for input to ECG apparatus 70. While the patient is at rest, cuff 38 is applied just above an elbow, and the pulse wave form sensor 40 its attached 1-3 cm distal to the cuff on the same arm. The pulse waveform signal is acquired by microcomputer 20 from apparatus 42 and displayed together with the ECG, on the physiological data display 22, where the quality of both ECG and pulse waveform signals are used as visual feedback to verify proper signal acquisition or to guide any required adjustment.

FIGS. 3A, 3B and 3C illustrate the technique by which the sample points on the composite pressure-time curve are determined, through the relationship between brachial arterial pressure, cuff pressure, the ECG QRS complex, and the detection of a pulse wave form distal to the cuff.

Two simplified cardiac cycles are shown with representative parameter values in FIGS. 3A-3C. In the first cardiac cycle, systolic pressure is 110 and cuff pressure is set to 100 Torr, while in the second cycle, systolic pressure is 115 and cuff pressure is set to 90 Torr Shown in FIG. 3A are the brachial pressure waveform, the cuff pressure, and the ECG waveform, indicating the relative timing of the QRS complex of each cardiac cycle and the resulting brachial pressure waveform.

Point A1 of cardiac cycle 1 occurs at the first instance during the cycle when brachial pressure exceeds cuff pressure. Referring to FIG. 3B, which depicts the pulse waveform produced by pulse wave form processor 42, it is noted that the pulse waveform abruptly rises at point B1, whose occurrence coincides in time with point A1 of FIG. 3A, as the blood pressure wave passes the cuff, i.e., breaks through, and causes arterial wall motion that is sensed by device 42.

The time delay from the QRS complex to the beginning of the abrupt rise of the pulse waveform, labeled T1 and having a value of 220 msec in FIG. 3B represents the time, after the QRS complex, when brachial arterial pressure reached 100 Torr. In FIG. 3C, which represents the composite pressure-time curve, point C1 has a pressure value of 100 Torr and a time of 220 msec, in accordance with the pressure and time values of points A1 and B1 above. It is noted that the time scale of FIG. 2C is in msec, whereas that of both FIGS. 3A and 3B is in seconds.

In similar fashion, in cardiac cycle 2, where systolic pressure is shown as 115 Torr and cuff pressure is shown as 90 Torr, points A2 and B2 correspond to the time when the blood pressure wave breaks through the cuff, which occurs at 180 msec after the QRS of cardiac cycle 2. In FIG. 3C, point C2 is shown at a pressure of 90 Torr and a time of 180 msec, in accordance with the pressure and time values of points A2 and B2 above. In actual implementation, each point on the composite pressure-time curve is determined by averaging together the delay times measured for a given cuff pressure maintained over a plurality of cardiac cycles.

While the patient is still in resting position, the operator causes the cardiac monitor 10 to commence measurement initialization. During initialization, prior to application of any pressure on cuff 38, the arterial pressure propagation time from heart to brachial artery is estimated, and the pulse waveform is characterized.

Cardiac monitor 20 is operated to measure the maximum and minimum pulse waveform values. Pulse waveform values MAXAMP and MINAMP are the respective average maximum and minimum values of the pulse waveform output of detector 42 during a plurality of cardiac cycles, preferably 10. MAXAMP is preferably obtained by averaging together the maximum amplitude value of the output of detector 42 from the aforementioned plurality of cardiac cycles, while MINAMP is preferably obtained by averaging together the minimum amplitude value of the output of detector 42 from each of the aforementioned plurality of cardiac cycles.

Figure 4:
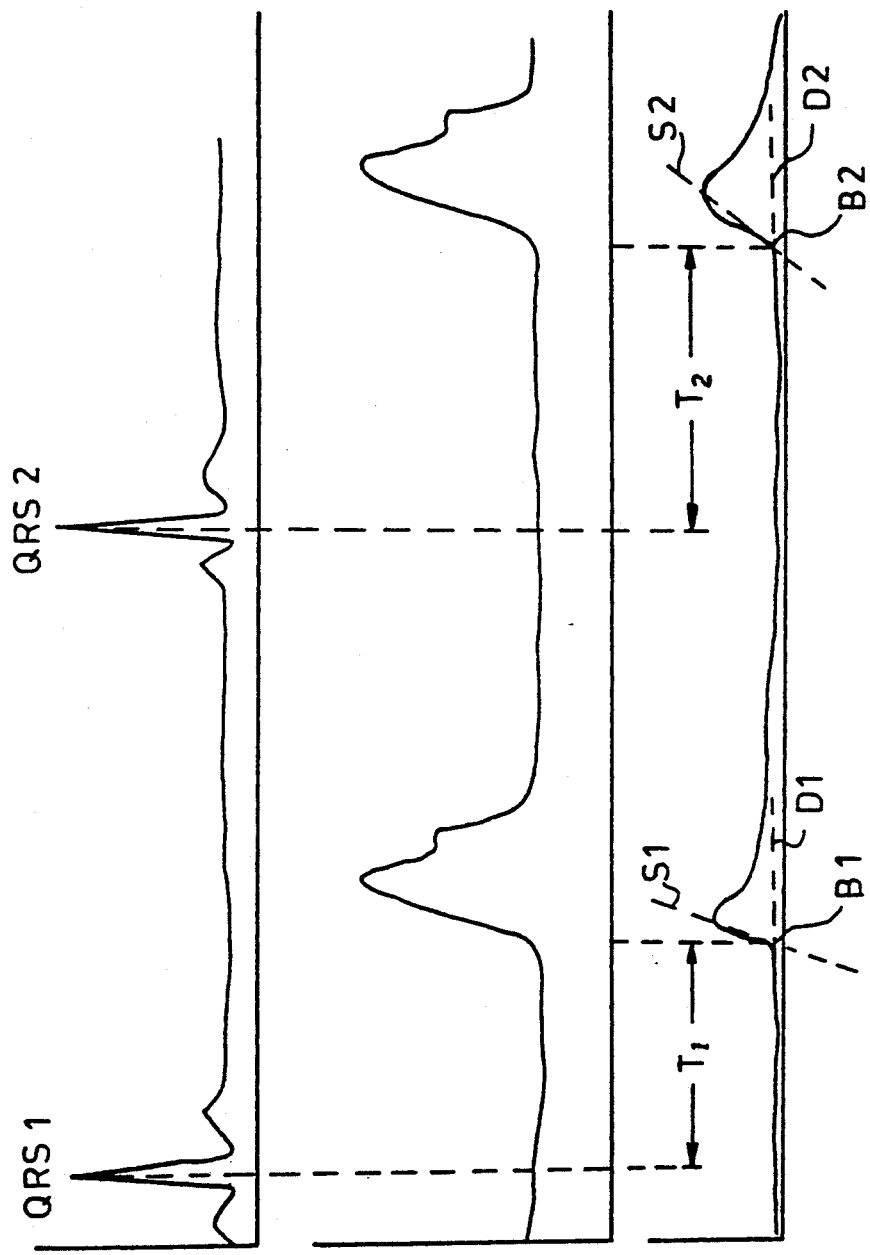
FIGS. 4A, 4B and 4C are a collection of idealized graphs of ECG, brachial arterial pressure and brachial arterial wall motion as a function of time, which are useful in understanding the operation of the apparatus of FIG. 1.

FIGS. 4A, 4B and 4C illustrate a method for calculating the propagation time, which is also used for calculating the breakthrough time referred to below and in Procedure ARRIVAL of FIG. 7. FIGS. 4A, 4B and 4C, respectively, show the ECG waveform brachial arterial pressure waveform, and pulse waveform for two idealized cardiac cycles. The propagation time is calculated by first detecting the steep upswing of the pulse waveform shown in 4C.

A regression line, labeled S1 in the first cycle and S2 in the second cycle, is fitted to the early portion of the upswing, preferably to the samples from the first 30 milliseconds of the upswing. A second regression line, labeled D1 in the first cycle and D2 in the second cycle, is fitted to the last portion of the waveform prior to the upswing, preferably to the samples during the last 30 milliseconds prior to the upswing. The time interval T1, from the R-wave of QRS 1 until the intersection point B1 between lines S1 and D1, is the arrival time of the pulse wave of cardiac cycle 1 at the pulse waveform sensor 40. Similarly, the time interval T2, from the R-wave of QRS 2 until point B2 is the arrival time of the pulse wave of cardiac cycle 2 at sensor 40. When determining propagation time, the above arrival times are preferably averaged together from a plurality of cardiac cycles, preferably 10 cycles.

The operator then causes the apparatus 30 to obtain the diastolic and systolic pressure values, and the heart rate, via microcomputer 20. A cuff pressure control algorithm, one embodiment of which illustrated in FIG.

5, uses the measured diastolic and systolic pressure values, and selects the pressures to which the cuff is to be inflated.

Figure 5:
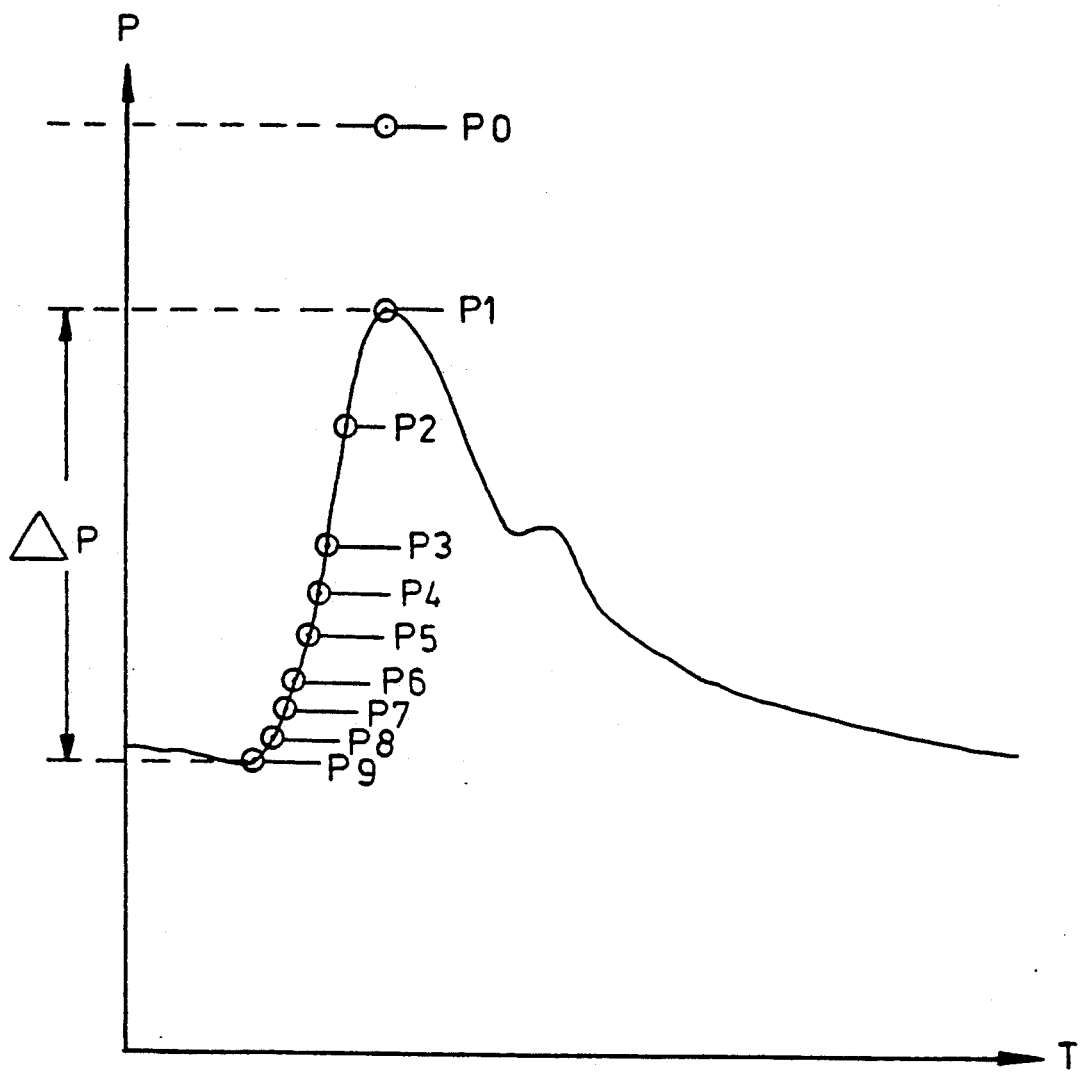
FIG. 5 illustrates one possible version of a cuff pressure control algorithm for optimal decrementing of cuff pressure.

In a particularly important characteristic of the present invention, the series of pressure values to be implemented by the cuff 38 are defined such that the largest number of pressure measurements are concentrated during the early ejection phase, typically defined as the phase between 100–125% of the end-diastolic pressure. An example optimization algorithm for defining the pressure values is illustrated in FIG. 5, wherein the pressures P0 through P9 are set as follows:
for DP=Systolic pressure—Diastolic pressure
P0—1.25 · Systolic
P1—Systolic pressure
P2—Systolic—0.25 · DP
P3—Systolic—0.50 · DP
P4—Systolic—0.45 · DP
P5—Systolic—0.75 · DP
P6—Systolic—0.85 · DP
P7—Systolic—0.90 · DP
P8—Systolic—0.95 · DP
P9—Diastolic pressure The number of points, and their precise dependence on systolic and diastolic pressure, may vary from the foregoing, so long as there are a plurality of points in the pressure range from the end-diastolic point to midway up the systolic rise, i.e., from diastolic pressure to (systolic—0.5 · DP). In response to an operator instruction to monitor 10, cuff 38 is inflated to pressure P0, and the pulse detector output used to verify occlusion of flow by the cuff.

The threshold for confirmation of occlusion is when the output amplitude of pulse waveform detector 42 is less than a fraction of the difference between aforementioned MAXAMP and MINAMP, preferably 0.05 ·(MAXAMP-MINAMP). If the original cuff pressure P0 does not reduce the output of detector 42 per above, the value of P0 is increased, preferably by 10% of its previous value, and the confirmation procedure repeated. The above is repeated until occlusion is confirmed or until P0 reaches a maximum of 150% of systolic pressure. Once occlusion is confirmed, the detected pulse waveform values are averaged together over a plurality of cardiac cycles, typically 10, to obtain an average baseline value AMP.

The operator then operates monitor 10 to commence the measurement of the pressure-time curve. Cuff pressure is reduced to value P1, intended to allow breakthrough only near the systolic peak. Microcomputer 20 analyses the pressure waveform signal in real time during the current cardiac cycle to determine if and when breakthrough occurs. Breakthrough is typically defined as the point when the waveform value first rises significantly above the baseline, which in the preferred embodiment is defined as a rise of more than three standard deviations above the aforementioned baseline average value AMP.

If and when breakthrough is detected, the method described above in determining propagation time is used to estimate the breakthrough time. The above procedure is repeated during at least 2, typically 5–10, cardiac cycles for the same cuff pressure setting, providing at least 2, typically 5–10, estimates of the breakthrough time for the pressure, from which mean and variance are calculated for said breakthrough time. Before proceeding to a new cuff pressure value, the set of breakthrough time estimates is reviewed, and outlying values (typically those lying more than three standard deviations from the mean) are excluded form the set, and a new final mean value calculated. The final mean value is the one stored in the pressure-volume curve for the cuff pressure value used.

Once the final pressure-time point has been determined for a given cuff pressure value, the cuff pressure is then reduced to the next value determined in the cuff pressure control algorithm, until the last value has been completed.

Figure 3:
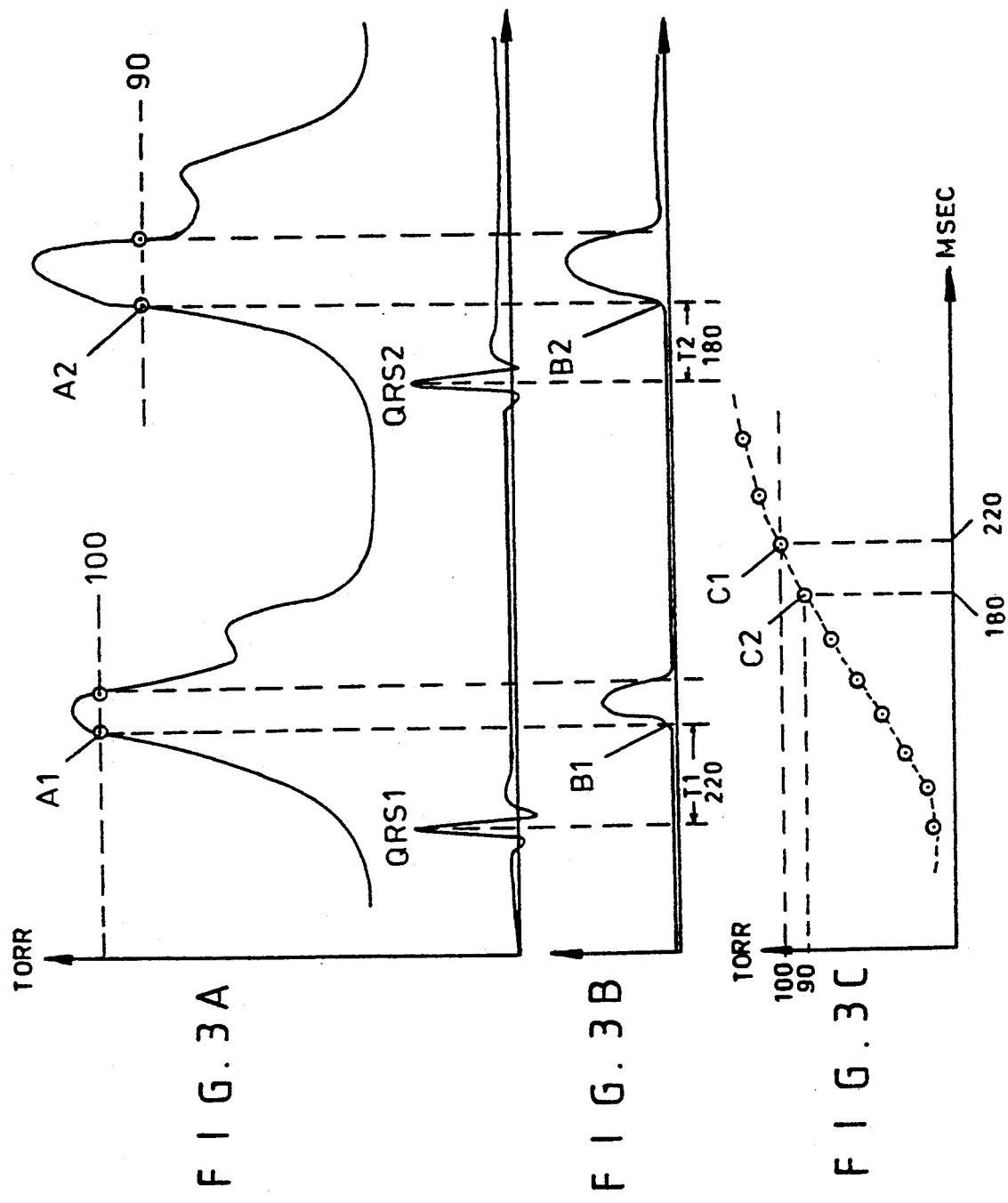
FIGS. 3A, 3B and 3C illustrate the derivation of points on a pressure-time curve using a cuff, an ECG, and a distal pulse wave form sensor.

It will be appreciated from a consideration of FIG. 3 that at low pressures, such as those close to the diastolic pressure, the above-mentioned method may be unreliable as the required standing column of blood is not well established prior to the onset of systole. Hence, the pressure-time value for onset of systole is taken to be the most recently measured diastolic pressure value and its time is taken to be the aforementioned propagation time determined when the patient was at rest.

The set of pressure values then obtained is interpolated typically by a piecewise polynomial curve fit by least squares minimization to provide estimated pressure values at any desired time point during the systolic portion of the cardiac cycle. The pressure curve a shown in FIG. 6B, which typically comprises an average of pressure values recorded over a multiplicity of cardiac cycles as described hereinabove, is then shifted by the amount of the propagation delay, thereby producing an estimated left ventricular pressure curve.

LEFT VENTRICULAR VOLUME DETERMINATION

Reference is now made again to FIG. 1. As noted above, in the preferred embodiment, the invention additionally comprises a field-of-view gamma camera 60, such one commercially available form Elscint of Haifa, Israel, and its associated CPU 62. The gamma camera 60 and CPU 62 measure the volume fo the left ventricle using gated radionuclide ventriculography according to the count rate method as described in "Left Ventricular Pressure-Volume Diagrams and End-systolic Pressure-Volume Relations in Human Beings," by McKay, R.G., et al., and published in *Journal of the American College of Cardiology*, vol. 3, 1984.

In accordance with a preferred embodiment of the invention, the R-wave detector 72 detects the R-wave of the ECG signal. Alternatively, if gamma camera 72 incorporates an ECG apparatus and associated QRS or R-wave detector, the QRS or R-wave is detected by the detector of the gamma camera.

Figure 6A:
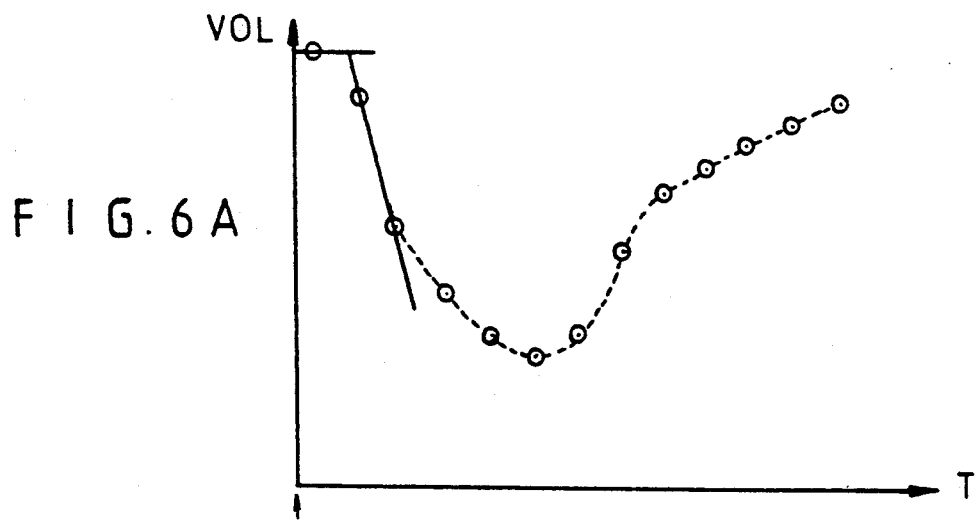
FIGS. 6A, 6B and 6C illustrate the acquisition and synchronization of composite volume and pressure curves, and the calculation of the resulting cardiac power curve, from which the cardiac power index (CPI) is derived.

A predefined amount of time later, typically 10–20 msec, the gamma camera 60 counts the number of gamma rays coming from the left ventricle during a predefined time frame, typically 5–10 msec. The gamma camera 60 repeats the measurement every typically 20–50 ms, producing sampled points on a curve of the left ventricular volume with time. The volume curve thus produced is typically synchronized to the QRS complex via the R-wave detector, and is illustrated in FIG. 6A.

Figure 6B:
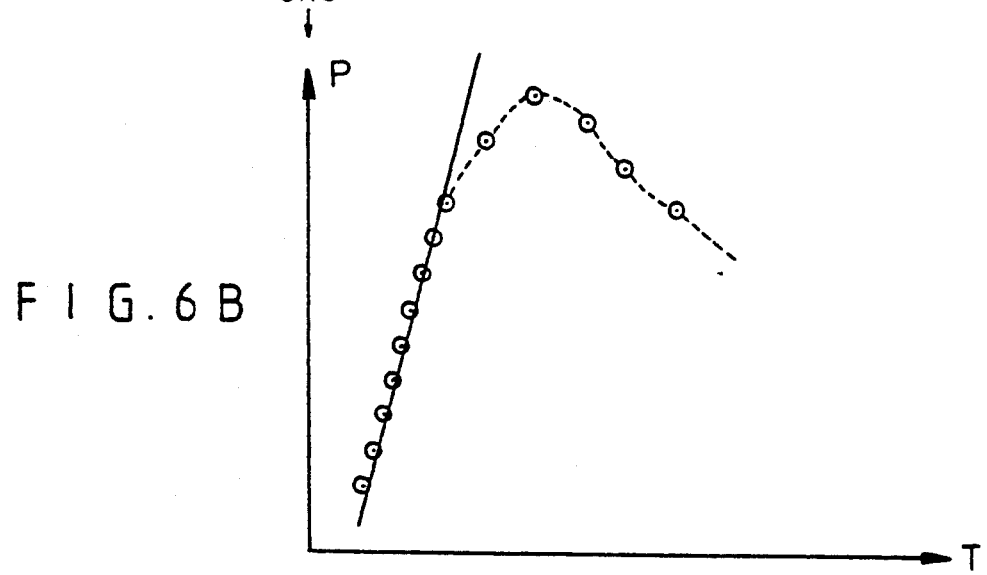
Figure 6C:
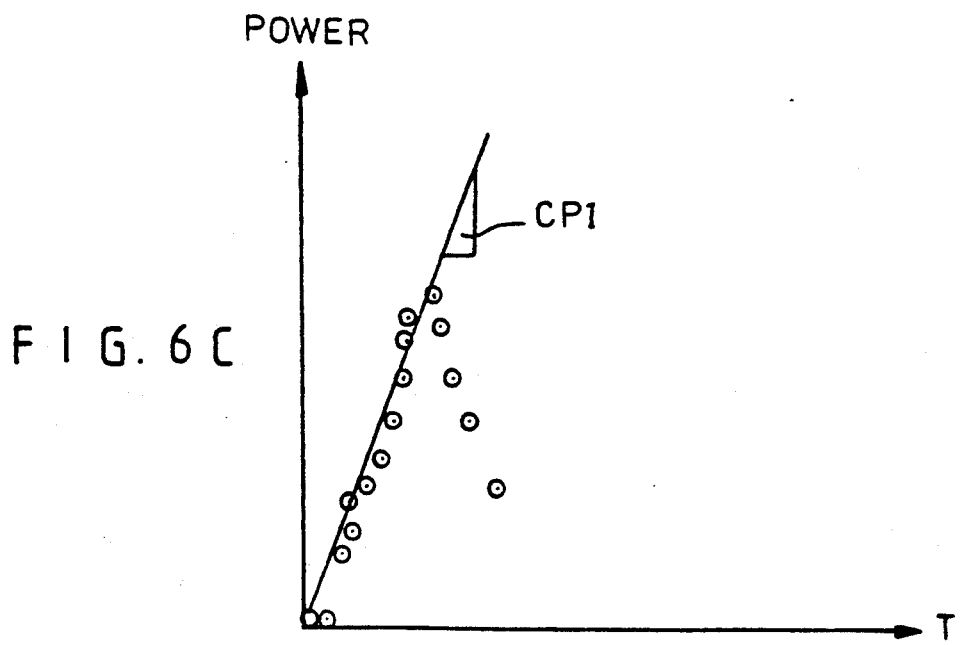

Typically, the volume curve will have only a few points and, thus, it is typically interpolated by least squares piecewise polynomial curve-fitting methods. Thus, an interpolated volume curve, illustrated in FIG. 6A, is calculated which has data at the same time points as the pressure curve calculated in accordance with the method described hereinabove. The cardiac power curve can thus be calculated from the volume curve and the pressure curve, as illustrated in FIGS. 6A, 6B and 6C.

CALCULATION OF CARDIAC POWER CURVE AND CPI

At a plurality of points throughout systole, typically 32 points, the product of the corresponding pressure and volume values is calculated. The time derivative of the product is typically estimated using a second order central difference method, to produce corresponding points on a cardiac power curve, illustrated in FIG. 6C. In the preferred embodiment, the CPI is calculated from the cardiac power curve values as follows:

A linear regression line is fitted to the points of said power curve between the start of systole and up to and including its maximum value. Any data points whose value lies more than two standard deviations from the linear regression line are excluded. After having excluded the outlying points, a new regression line is calculated, and its slope is used as the final CPI value.

The entire sequence of operation of monitor 10, as described above, is summarized in FIG. 7.

Figure 8:
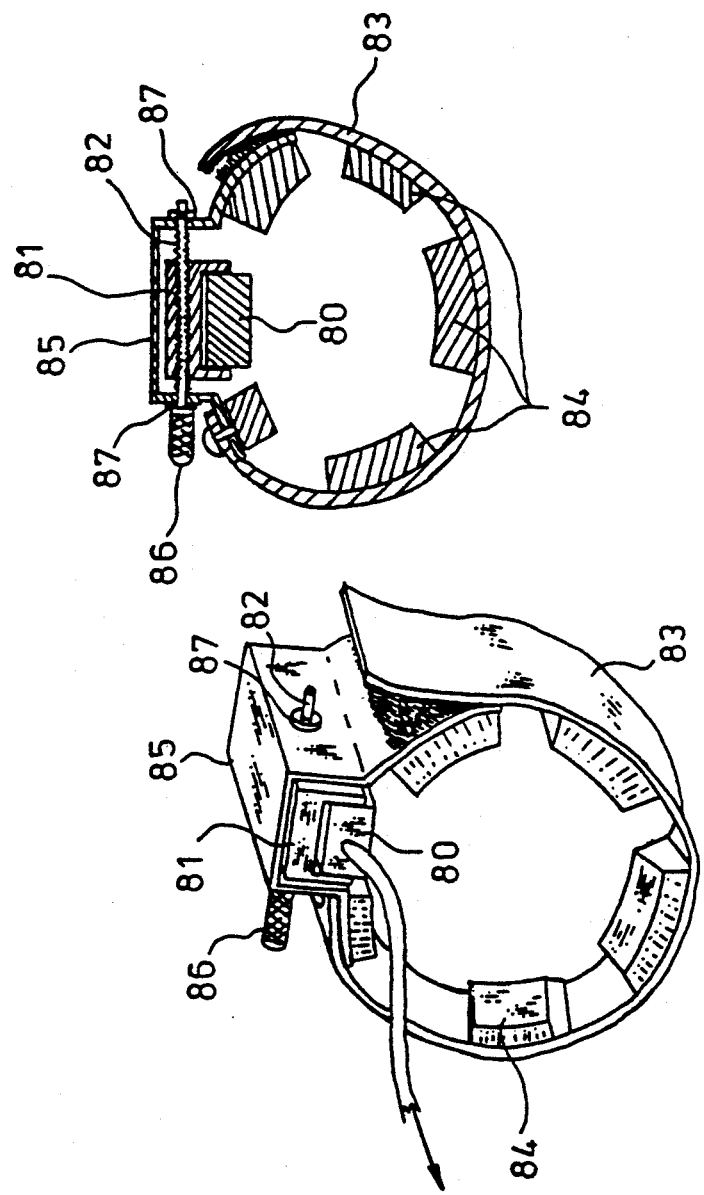
FIG. 8 shows a specific embodiment of a pulse wave form sensor together with holding means.

FIG. 8 shows a pulse waveform sensor 40 together with its mounting means. The sensor 40 is a Doppler ultrasound arterial blood flow sensor and comprises a Doppler ultrasound transducer 80 which is formed as a flat package. This enables a stable, compact mounting on the patient's arm. The Doppler crystals are mounted so as to provide a fixed angle of illumination, typically 30 to the horizontal.

The transducer is held by a transducer mount 81 which is adjustably supported in a bracket 85, the two legs of which serve for the attachment of a strap 83 which is put around the arm of a patient. The strap 83 can be fastened around the arm in a tight manner by an adhesive-free connection of its ends, for instance by means of Velcro material. At its inner side, the strap has a plurality of pieces 84 of a compressible material which serve for the absorption of shocks and movements.

After initial attachment of the transducer in approximate location, a fine adjustment of transducer position is made by an adjustment means including a screw strap 82 extending through corresponding bores in the bracket 85 and the transducer mount 81 and through two retaining rings 87 on both sides of the bracket. The screw shaft can be manually operated by a knob 86 at its one end. By turning the knob 86, the mount 81 and then the transducer 80 is moved transversely with respect to the arm of the patient.

Figure 9:
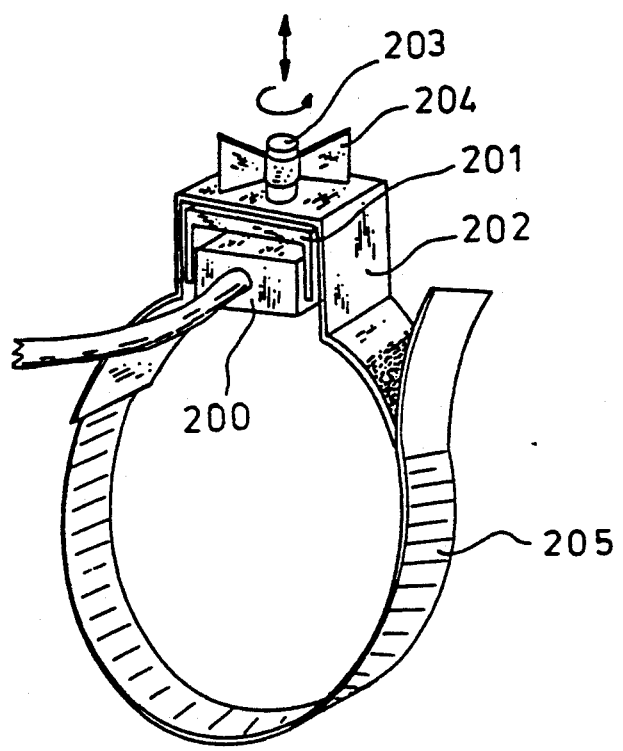
FIG. 9 shown another embodiment of the holding means for the pulse wave form sensor.

This embodiment allows a reliable attachment to the arm without adhesives and maintenance of adequate pressure of transducer against the desired skin location Another embodiment of the mounting surface for the transducer is shown in FIG. 9. The transducer 200 is identically shaped as in FIG. 8. It is also held by a transducer mount 201 having the shape of an inverted U. According to this embodiment, the mount can be moved vertically in the drawing so that the pressure with which the transducer is pressed against the arm can be adjusted. This is realized by means of an adjustment screw 203 which can be manually turned (at 204) and which extends through a screw bore in a bracket 202. Accordingly, by turning the screw, the distance between the mount 201 and the bracket 202 is varied and the transducer package is thus pressed against the arm.

As in the embodiment of FIG. 8, the two legs of the bracket 202 serve for the attachment of a strap 205 which can be put around a patient's arm. The strap can be fastened in a tight manner by means of a similar connection as shown in FIG. 8.

Figure 10:
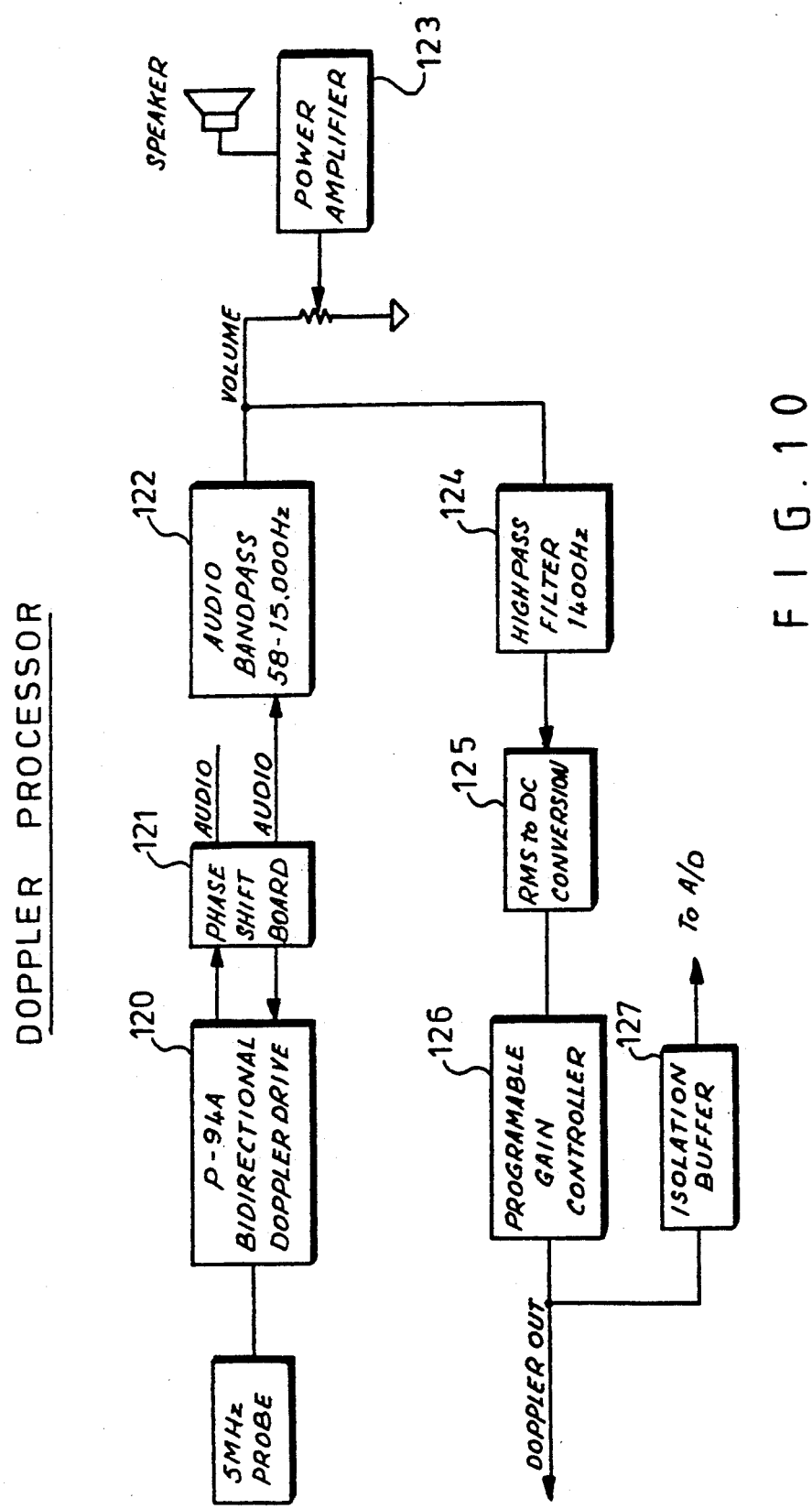
FIG. 10 is a block diagram of a processor for the pulse wave form sensor.

It is now referred to an embodiment of a pulse wave form processor 42 of which a block diagram is shown in FIG. 10. The processor has the following components:

120 BIDIRECTIONAL DOPPLER PROBE, model MEDASONICS P 94-A, is a 5 MHz Doppler blood flow transducer connected to the driving circuit.

PHASE SHIFT BOARD, MEDASONICS p.n. 109-0051-010, separates the sounds of the advancing blood flow, providing two high level audio outputs.

AUDIO BAND PASS, passes the frequencies between 70 Hz and 15,000 Hz, suppressing noise, especially the 50/60 Hz "hum".

123 POWER AMPLIFIER provides the speaker drive and volume control from the front panel.

124 HIGH-PASS FILTER separates the high frequencies from the audio signal. The blood breakthrough generates high frequencies (beyond 1400 Hz). This filter also attenuates the sound generated by the receding flow which has lower frequencies.

125 RMS to DC CONVERSION measures the power of the high frequency spectrum by converting the total RMS (root mean square) into a proportional DC voltage.

126 PROGRAMMABLE GAIN CONTROLLER, allows amplification of the RMS value under computer control. Three bits set eight levels of gain. The processed Doppler signal is available at the BNC output connector.

127 ISOLATION BUFFER, transfers the processed Doppler signal to the A/D converter which is isolated, according to patient safety standards.

According to this embodiment, the processor provides an analog output which is preferably proportional to the total rapid blood flow, i.e., the portion of the blood flow detected by sensor 40 which is flowing with significant velocity. The processor produces an output to an A/D converter which is proportional to the root mean square (RMS) amplitude of the Doppler audio shift frequencies above the smaller or 300 Hz of a frequency equal to the multiple of the Doppler carrier frequency and the factor $6 \times 10^{-5}$.

Figure 11A:
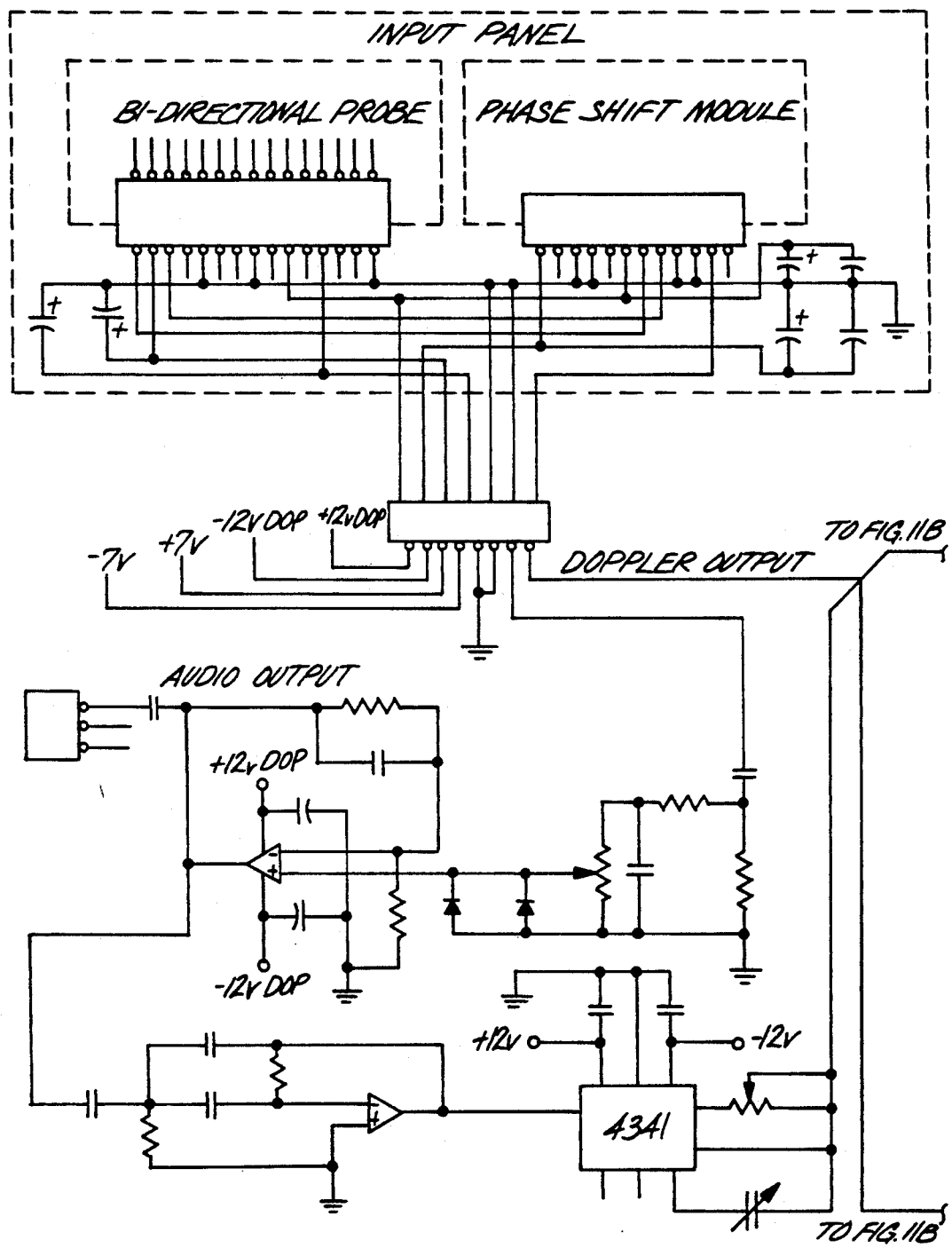
FIGS. 11a and b are an exact circuit of the processor according to FIG. 10.

FIG. 11 shows an exact circuit of the processor according to FIG. 10.

Figure 13A:
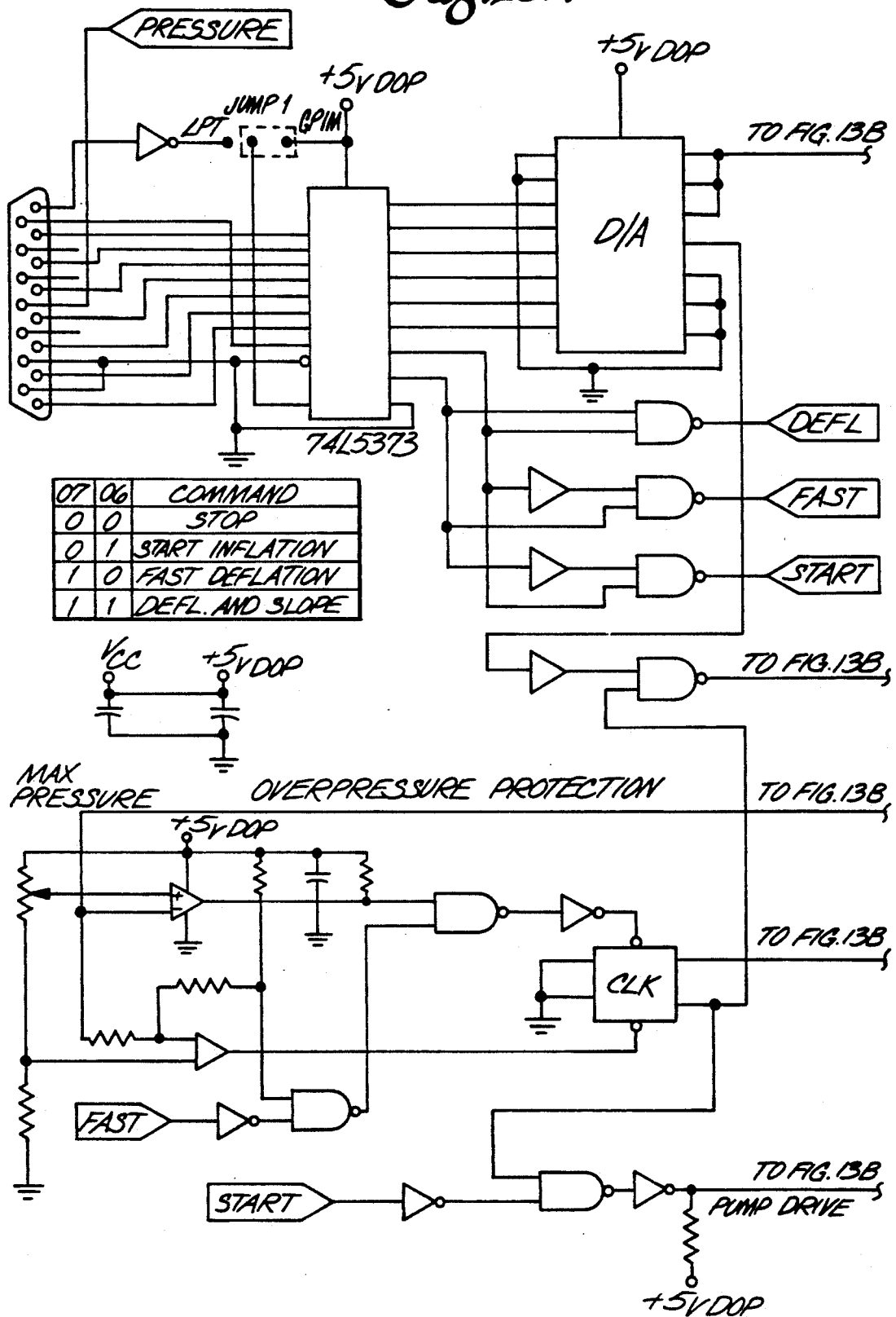
FIGS. 13A and B are an exact circuit of the cuff pressure control unit according to FIG. 12.
Figure 13B:
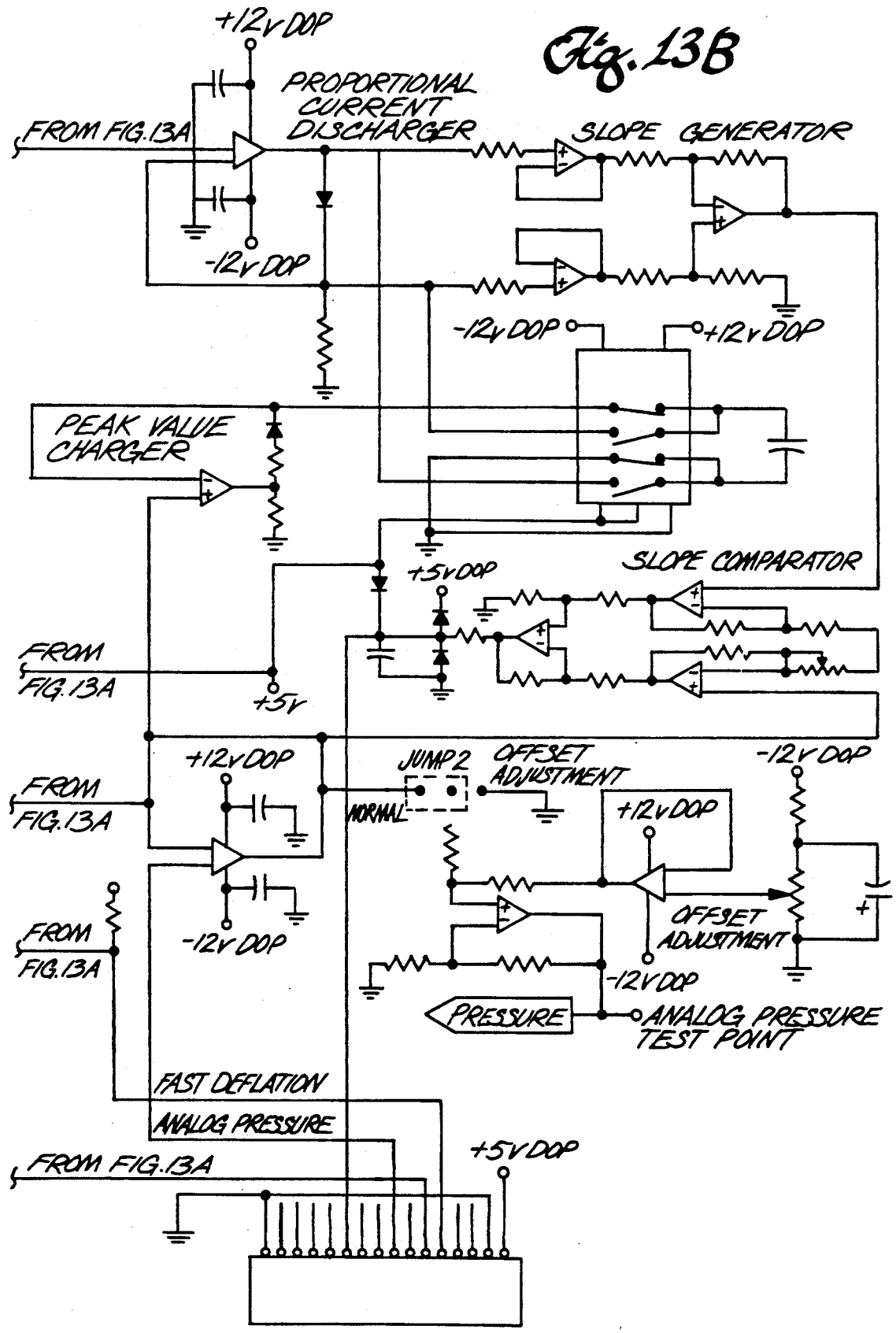

FIG. 12 is a block diagram of a cuff pressure control unit, i.e., of the pump controller 36 shown in FIG. 1. An exact circuit of this unit is shown in FIG. 13.

The cuff pressure controller has the following components:

101 PARALLEL INTERFACE, configured as an 8-bit parallel port, D-15 connector, receives the commands from the PC (Dell Computer). The available commands are:
INFLATE
STOP
SLOW DEFLATION OF GIVEN RATE
FAST DEFLATION 102 8 BIT LATCH stores the received command, controlled by STROBE pulse.

103 DIGITAL TO ANALOG CONVERTER uses the six most significant bits to generate 64 voltage steps (2.56V full scale, 40 mv per bit).

VOLTAGE CONTROLLED CURRENT SOURCE converts the constant voltage into constant current, according to:

current=input voltage/20k ohm which means 2 microamp per bit (126 microamp max).

105 CAPACITOR DISCHARGER is a circuit capable of discharging a 1000 μf capacitor, with constant current provided by block 104, in a floating mode (none of the terminals connected to the ground). Due to the constant current discharge the voltage across the capacitor falls with a constant rate given by:

dv=1/c time · current which gives a min of 2 mv/sec and a max of 126 mv/sec.

106 COMMAND DECODER receives the two least significant bits of the received byte, decoding the four basic commands: inflate, stop, quick deflate and deflation of given rate.

107 CHARGE/DISCHARGE SWITCH connects the low leakage capacitor (used as sample & hold) to the charge of discharge circuit. The analog switch is DPDT type.

108 LOW LEAKAGE CAPACITOR, 1000 μf, is used as a voltage memory. The voltage across the capacitor follows the actual cuff pressure value. Discharging it with a constant current generates a linear decreasing voltage.

109 CAPACITOR CHARGER & COMPARATOR, determines the voltage across the capacitor to follow the actual cuff pressure value. The value is received from the Bosch unit as 1 volt per 100 mm Hg pressure.

110 QUICK RELEASE CIRCUIT is a driver for the quick release valve of the Bosch unit. Quick deflation occurs upon receiving the corresponding command or when the pressure reaches the maximum allowed value (300 mm Hg).

111 OVER PRESSURE PROTECTION is an emergency circuit which completely deflates the cuff at 300 mm Hg pressure. This factory value can be changed by use of an internal potentiometer.

112 VOLTAGE COMPARATOR is the feedback loop controlling the Bosch's deflation valve. During the slow deflation, the capacitor is discharged with a programmed constant current. The voltage across the capacitor is a linear descending ramp. The comparator compares this voltage with the actual pressure value. The amplified error value drives the deflation valve. As a result the pressure decreases at the programmed rate.

113 OFFSET CORRECTION, allows the calibration of analog pressure value against a standard manometer.

The cuff pressure controller has the following principle of operation:

Upon receiving (through the parallel port) the command INFLATE, the pump is energized and inflates the cuff until the STOP command is received. During the inflation the capacitor is accurately charged to a voltage value equal to the actual pressure.

The SLOW DEFLATE command contains six bits which finally are converted into a constant current. This current discharges the capacitor generating an internal built-in linear voltage ramp. The comparator compares this voltage to the pressure value, amplifying the difference. The error voltage drives the deflation valve forcing the pressure to follow the ramp. With the described values the minimum deflation rate is 0.2 mm Hg per sec and the maximum 12.6 mm Hg per sec.

The QUICK DEFLATION command deflates the cuff immediately.

The STOP command freezes the cuff pressure to the last value.

It will be appreciated by persons skilled in the art that the present invention is not limited to what has been particularly shown and described hereinabove. Rather, the scope of the present invention is defined only by the claims which follow.

What is claimed is:

1. A method for noninvasively measuring the value of cardiac power index as a descriptor of performance of a heart comprising the steps of:
   noninvasively measuring the left ventricular pressure of the heart with reference to time; the step of measuring the left ventricular pressure comprising the steps of measuring the arrival times of cardiac pressure pulses at a given arterial site displaced form the heart at a plurality of pressure values;
   noninvasively measure the left ventricular volume of the heart with reference to time;
   determining the work performed by the left ventricle as the product of the left ventricular pressure and the left ventricular volume as a function of time;
   determining the power of the left ventricle as the time derivative of said product; and
   determining the slope fo the time derivative as it rises during the interval from the onset of systole to the moment of maximum power, thereby to provide a value of the cardiac power index.

2. A method according to claim 1 in which the step of measuring the left ventricular pressure also comprises the step of:
   concentrating the largest number of pressure measurements in the interval during the early ejection phase of the left ventricle.

3. A method according to claim 2 in which the step of measuring the left ventricular pressure also comprises the step of measuring the arrival times of cardiac pressure pulses at the given site during the time period during which the left ventricular pressure rises from 100% to 125% of the end-diastolic value.

4. A method according to claim 1 and also comprising the step of displaying real-time electrocardiogram and blood pressure wave forms on a continuously updated basis.

5. A method according to claim 4 and also comprising the steps of displaying simultaneously and together with said electrocardiogram and pressure wave forms, left ventricle pressure and corresponding left ventricular volumetric values.

6. A method according to claim 1 including the step of measuring, during one or more cardiac cycles, the arrival time for a selected occlusive pressure, and storing the measured times.

7. A method according to claim 1 and wherein the step of measuring the time of arrival includes the step of rejecting time values having unacceptable variance.

8. A method according to claim 1 and wherein the step of measuring the time of arrival also includes the step of statistical averaging of several acceptable time measurements to reduce the effects of beat-to-beat variance, artifactual signals and noise.

9. A method according to claim 1 and wherein said step of measuring left ventricular volume includes the step of taking at least one measurement within 15 msec of QRS.

10. A method according to claim 9 and wherein said step of measuring left ventricular volume includes the step of carrying out multiple volume measurements within 40 msec of each other.

11. A method according to claim 10 including steps of measuring the systolic and diastolic blood pressure.

12. A method according to claim 1 and also comprising the step of calculating the cardiac power index as the slope of the best least squares regression fit to an entire set of instantaneous power values up to a maximum power point, excluding points whose values lie outside the range of variance that is commensurate with the other points.

13. Apparatus for noninvasively measuring the value of cardiac power index as a descriptor of performance of a heart comprising:
   means for noninvasively measuring the left ventricular pressure of the heart with respect to time, including means for measuring the arrival times of cardiac pressure pulses at a given arterial site displaced from the heart;
   means for noninvasively measuring the left ventricular volume of the heart with respect to time;
   means for determining the work performed by the left ventricle as the product of the left ventricular pressure and the left ventricular volume as a function fo time;
   means for determining the power of the left ventricle as the time derivative of said product; and
   means for determining the slope of the time derivative as it rises from the onset of systole to the time of maximum power of the left ventricle, thereby to provide a value of the cardiac power index.

14. Apparatus according to claim 13 in which the means for measuring the left ventricular pressure also comprises means for concentrating the largest number of pressure measurements in the interval during the early ejection phase.

15. Apparatus according to claim 14 in which the means for measuring the left ventricular pressure also comprises means for measuring the arrival times of cardiac pressure pulses at the given site during the time period during which the left ventricular pressure rises form 100% to 125% of the end-diastolic value.

16. Apparatus according to claim 14 and also comprising means for displaying real-time electrocardiogram and blood pressure wave forms on a continuously updated basis.

17. Apparatus according to claim 16 including means for displaying, simultaneously and together with said electrocardiogram and pressure wave forms, left ventricle pressure and corresponding left ventricular volumetric values.

18. Apparatus according to claim 17 and further comprising means for measuring, during at least one cardiac cycle the arrival time for a selected occlusive pressure, and for storage of the measured ties.

19. Apparatus according to claim 18 and wherein the means for measuring the time of arrival includes means for rejecting time values having unacceptable variance.

20. Apparatus according to claim 18 and wherein the means for measuring the time of arrival also includes means for statistical averaging of several acceptable time measurements to reduce the effects of beat-to-beat variance, artifactual signals and noise.

21. Apparatus according to claim 20 and wherein said means for measuring left ventricular volume includes means for taking at least one measurement within 15 msec of QRS.

22. Apparatus according to claim 21 and wherein said means for measuring left ventricular volume includes means for carrying th systolic and diastolic blood pressure.

23. Apparatus according to claim 20 and further including means for measuring the systolic and diastolic blood pressure.

24. Apparatus according to claim 23 and also comprising means for calculating the cardiac power index as the slope of the best least squares regression fit to an entire set of instantaneous power values up to a maximum power point, excluding points whose variance is not commensurate with the other points.

25. Apparatus according to claim 13 wherein said means for noninvasively measuring left ventricular pressure includes a pulse wave sensor and a pulse wave processor operative to reject motion artifact in the measurement of left ventricular pressure.

26. Apparatus according to claim 25 and wherein said means for detecting the arrival fo the cardiac pressure wave at a given site is a Doppler ultrasound arterial wall motion sensor.

27. Apparatus according to claim 25, wherein said means for detecting the arrival fo the cardiac pressure wave at a given arterial site is a Doppler ultrasound blood flow sensor.

28. Apparatus according to claim 27 characterized by means for rejecting motion artifact in the measurement of left ventricular pressure, said means comprising a Doppler sensor holder and means for rejecting low frequencies from the Doppler audio shift spectrum.

29. Apparatus according to claim 27, wherein said Doppler ultrasound sensor is held by an armband mount comprising an adjustable sensor fixed to an adjustable attachment strap.

30. Apparatus according to claim 27, wherein said Doppler ultrasound sensor is formed as a flat package with Doppler crystals mounted so as to provide fixed angle of illumination of about 30° to horizontal.

31. Apparatus according to claim 25, wherein said pulse wave processor includes a high-pass filter separating the high frequencies form the audio signal and a RMS-amplitude-to-DC-converter measuring the power of the high frequency spectrum by converting the total RMS value into a proportional DC voltage.

32. A method for reliably measuring performance of a heart under resting and/or exercise stress conditions to enable measurement of a cardiac power index, the method comprising the steps of
   noninvasively measuring, through at least a portion of each of a selected number of cardiac cycles, the left ventricular pressure of the heart, including measuring at a plurality of pressure values the times of arrival of cardiac pressure pulses at a given arterial site displaced from the heart,
   noninvasively measuring, through corresponding portions of a corresponding number of cardiac cycles, the left ventricular volume of the heart,
   determining the product of the left ventricular pressure and left ventricular volume as a function of time, thereby to determine the work performed by the left ventricle, determining the time derivative of said product, thereby to determine the left ventricular power, and determining the slope of the time derivative as it rises during the interval from the onset of the systole to the moment of maximum power, thereby to provide a value of the cardiac power index for that heart.

33. Apparatus for reliably measuring performance of a heart under resting and/or exercise stress conditions to enable measurement of a cardiac power index, the apparatus comprising mans for noninvasively measuring, through at least a portion of each of a selected number of cardiac cycles, the left ventricular pressure of the heart, including means for measuring at a plurality of pressure values the times of arrival of cardiac pressure pulses at a given arterial site displaced from the heart, means for noninvasively measuring, through corresponding portions of a corresponding number of cardiac cycles, the left ventricular volume of the heart, means for determining the work performed by the left ventricle as the product of the left ventricular pressure and left ventricular volume as a function of time, means for determining the power of the left ventricle as the time derivative of said product, and means for determining the slope of the time derivative as it rises between the onset of systole to the point of maximum power, thereby to provide a value of the cardiac power index for that heart.

34. A method for reliably measuring performance of a heart under resting and/or exercise stress conditions to enable measurement of a cardiac power index, the method comprising the steps of:

noninvasively measuring, through at least a portion of each of a selected number of cardiac cycles, the left ventricular pressure of the heart, including measuring at a plurality of pressure values the times of arrival of cardiac pressure pulses at a given arterial site displaced from the heart, noninvasively measuring, through corresponding portions of a corresponding number of cardiac cycles, the left ventricular volume of the heart, effectively representing the variation of left ventricular work with time through corresponding portions of a corresponding number of cardiac cycles, effectively representing as a curve the power of the left ventricle during at least said portion of said cycles, and determining a value of the cardiac power index for that heart as the rate of change of left ventricular power between the onset of systole and the time of maximum power.

35. A method for noninvasively determining the cardiac power index of a living heart, the index being defined as the second time derivative of the work performed by the left ventricle of the heart between the onset of systole and a point of maximum left ventricular power, the method comprising the steps of noninvasively measuring, through at least a portion of each of a selected number of cardiac cycles, the left ventricular pressure of the heart, including measuring at a plurality of pressure values the times of arrival of cardiac pressure pulses at a given arterial site displaced from the heart, noninvasively measuring, through corresponding portions of a corresponding number of cardiac cycles, the left ventricular volume of the heart and determining the value for the Cardiac Performance Index on the basis of the measured values for left ventricular pressure and left ventricular volume.

* * * * *

UNITED STATES PATENT AND TRADEMARK OFFICE
CERTIFICATE OF CORRECTION

PATENT NO. : 5,199,438

DATED : April 6, 1993

INVENTOR(S) : Andrew L. Pearlman

It is certified that error appears in the above-indentified patent and that said Letters Patent is hereby corrected as shown below:

On the title page: Item

[56] References Cited, U.S. PATENT DOCUMENTS, change "4,493,210" to -- 4,493,216 --.

Item [57]
Abstract, line 11, change "form" to -- from --.

Column 2, line 12, before "pressure" delete "brachial".

Column 7, line 52, change "Torr Shown" to
-- Torr. Shown --.

Column 9, line 18, change "0.45" to -- 0.65 --.

Column 10, line 2, change "form" to -- from --.
Column 10, line 24, after "curve" change "a" to -- as --.
Column 10, line 38, after "volume" change "fo" to -- of --.

Column 11, line 30, change "30" to -- 30° --.

Column 12, line 12, before "PHASE" insert -- 121 --.
Column 12, line 16, before "AUDIO" insert -- 122 --.

Column 13, line 1, before "VOLTAGE" insert -- 104 --.
Column 13, line 17, change "dv=1/c time·current" to --
dv=1/c·time·current --.

UNITED STATES PATENT AND TRADEMARK OFFICE
CERTIFICATE OF CORRECTION

PATENT NO. : 5,199,438

DATED : April 6, 1993

INVENTOR(S) : Andrew L. Pearlman

It is certified that error appears in the above-indentified patent and that said Letters Patent is hereby corrected as shown below:

In the Claims:

Column 14, line 25, change "form" to -- from --.
Column 14, line 33, after "slope" change "fo" to -- of --.

Column 15, line 11, after "including" insert -- the --.
Column 15, line 33, before "time" change "fo" to -- of --.
Column 15, line 50, change "form" to -- from --.
Column 15, line 55, before "including" insert -- and --.
Column 15, line 63, change "ties" to -- times --.
Column 15, line 67, change "claim 18" to -- claim 19 --.

Column 16, lines 10,11, delete "th systolic and diastolic blood pressure" and insert therefor -- out multiple volume measurements within 40 msec of each other --.
Column 16, line 27, after "arrival" change "fo" to -- of --.
Column 16, line 32, after "arrival" change "fo" to -- of --.
Column 16, line 50, change "form" to -- from --.

Column 17, line 16, change "mans" to -- means --.

Signed and Sealed this

Twenty-second Day of March, 1994

Attest:

BRUCE LEHMAN

*Attesting Officer*  *Commissioner of Patents and Trademarks*